United States Patent
Sato et al.

(10) Patent No.: US 7,800,060 B2
(45) Date of Patent: Sep. 21, 2010

(54) PATTERN MEASUREMENT METHOD AND PATTERN MEASUREMENT SYSTEM

(75) Inventors: Hidetoshi Sato, Hitachinaka (JP);
Ryoichi Matsuoka, Yotsukaido (JP);
Takumichi Sutani, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 245 days.

(21) Appl. No.: 12/182,810

(22) Filed: Jul. 30, 2008

(65) Prior Publication Data
US 2009/0032707 A1 Feb. 5, 2009

(30) Foreign Application Priority Data
Jul. 31, 2007 (JP) .............................. 2007-199586

(51) Int. Cl.
*G01N 23/00* (2006.01)
*G21K 7/00* (2006.01)

(52) U.S. Cl. ..................... 250/307; 250/306; 250/310; 250/311; 250/559.46; 250/359.1; 250/492.2; 382/143; 382/144; 382/145; 356/237.1

(58) Field of Classification Search ................. 250/306, 250/307, 310, 311, 359.1, 559.46, 492.2; 382/143–145; 356/237.1
See application file for complete search history.

(56) References Cited

U.S. PATENT DOCUMENTS

| | | | |
|---|---|---|---|
| 6,868,175 B1 | 3/2005 | Yamamoto et al. | |
| 7,062,396 B2 * | 6/2006 | Ogawa | ........................ 702/85 |
| 7,660,455 B2 * | 2/2010 | Yamamoto et al. | .......... 382/141 |
| 7,664,308 B2 * | 2/2010 | Isomura | ...................... 382/144 |
| 7,679,055 B2 * | 3/2010 | Sutani et al. | ................ 250/307 |
| 2002/0015518 A1 | 2/2002 | Matsuoka | |
| 2006/0193508 A1 | 8/2006 | Sutani et al. | |
| 2006/0288325 A1 | 12/2006 | Miyamoto et al. | |
| 2008/0024601 A1 | 1/2008 | Sato et al. | |
| 2009/0039263 A1 * | 2/2009 | Matsuoka et al. | ........... 250/311 |

FOREIGN PATENT DOCUMENTS

| | | |
|---|---|---|
| JP | 2001-338304 A | 12/2001 |
| JP | 2002-31525 A | 1/2002 |
| JP | 2006-234688 A | 9/2006 |

* cited by examiner

*Primary Examiner*—Jack I Berman
*Assistant Examiner*—Meenakshi S Sahu
(74) *Attorney, Agent, or Firm*—Crowell & Moring LLP

(57) ABSTRACT

Easily and correctly measuring a dimension of a pattern of a photomask or of an OPC pattern of the photomask.

A pattern measurement method of the present invention includes steps of obtaining both a standard pattern corresponding to a predetermined pattern and a measurement point specified in advance; setting a measurement area so that it includes two straight line segments on both sides of the measurement point among outlines of the standard pattern; and measuring a dimension between two contours of the scanned image of the predetermined pattern in the measurement area by superposing the measurement area on the scanned image of the predetermined pattern. The measurement area is set so as not to include portions near corner portions connected to two line segments.

17 Claims, 8 Drawing Sheets

PATTERN MEASUREMENT METHOD AND PATTERN MEASUREMENT SYSTEM

BACKGROUND OF THE INVENTION

1. Field of the Invention

The present invention relates to a pattern measurement method and a pattern measurement system, and especially relates to a method and system for measuring a pattern from a scanned image obtained by a scanning electron microscope.

2. Description of the Related Art

In a manufacturing process of a semiconductor, generally, a circuit pattern on a semiconductor integrated circuit is inspected. One of an inspection method of the circuit pattern is that using Computer Aided Design (CAD) data being design data of the circuit pattern, as a standard pattern. In this method, the circuit pattern is evaluated by comparing a scanned image of an actually formed pattern with the CAD data.

Japanese Patent Application Laid-Open (JP-A) No. 2001-338304 (corresponding to U.S. Pat. No. 6,868,175) and JP-A No. 2002-31525 (corresponding to US2002/0015518) disclose to perform edge detection for each of a pattern image of an inspection object and the standard pattern, and compares the detected edges to detect a variation amount of the pattern with respect to the design data. Also, JP-A No. 2006-234588 (corresponding to US2006/0193508) discloses a method of setting a standard position regarding positioning between the design pattern and an actual pattern image to detect the pattern variation amount in greater detail.

Recently, due to a minute pattern of the semiconductor integrated circuit, a proximity effect of light in a photolithography technique becomes problematic. The proximity effect of light is a phenomenon in which a shape of the actually formed pattern is different from a shape of a mask pattern, when exposing the pattern to transfer. This is because a diffraction effect of light occurs when a pattern width is minute.

In order to eliminate the proximity effect of light to obtain a desired pattern, the mask pattern is corrected. This is referred to as an optical proximity correction (OPC). In the OPC technology, a light intensity distribution of an image passing through the mask pattern and being reduced-projected on a wafer is calculated, or ruled to change mask pattern data. Thereby, the desired pattern just as the design data may be obtained on the wafer. In general, the mask pattern changed by the OPC technology is referred to as an OPC pattern, and a dimension of the OPC pattern is often measured in the manufacturing process of the mask.

SUMMARY OF THE INVENTION

In the manufacturing process of the photomask, the dimension of the pattern of the photomask is measured. When the dimension of the pattern of the photomask being measured, it is required to set a measurement area. Conventionally, it has been difficult to adequately set the measurement area.

Further, in the manufacturing process of the photomask, it is required to measure the dimension of an OPC pattern of the photomask. In this case also, it is difficult to adequately set the measurement area. This is because it is difficult to select a desired measurement area from the OPC pattern when a shape of the OPC pattern is complicated.

An object of the present invention is to provide a pattern measurement method and a pattern measurement system capable of easily and correctly measuring the dimension of the pattern of the photomask or of the OPC pattern of the photomask.

The pattern measurement method of the present invention includes steps of obtaining both a standard pattern corresponding to a predetermined pattern and a measurement point specified in advance; setting a measurement area so that it includes two straight line segments on both sides of the measurement point among outlines of the standard pattern; and measuring a dimension between two contours of the scanned image of the predetermined pattern in the measurement area by superimposing the measurement area on the scanned image of the predetermined pattern.

According to the present invention, the measurement area is provided so as not to include portions near corner portions connected to the two line segments.

According to the present invention, the dimension of the pattern of the photomask or of the OPC pattern of the photomask is easily and correctly measured.

DESCRIPTION OF THE REFERENCE NUMERALS

Figure 1:
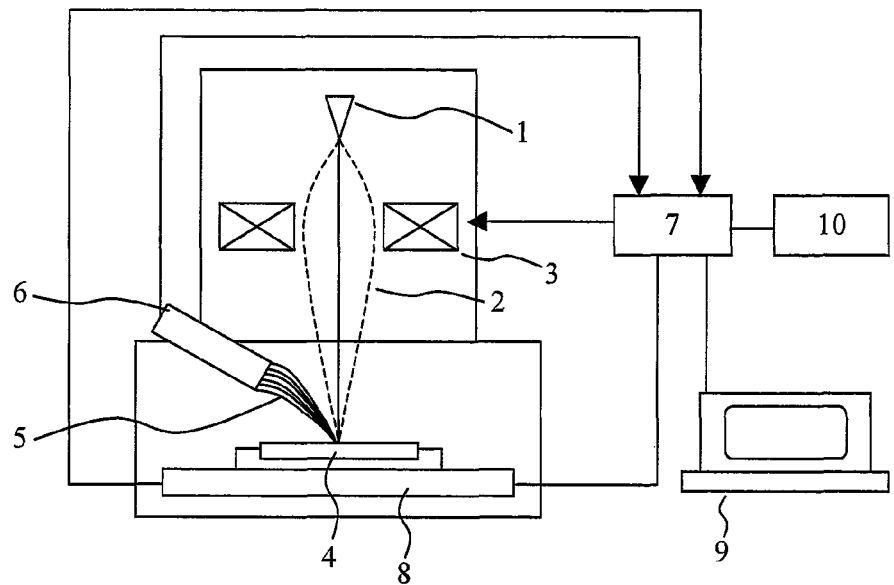
FIG. 1 is a view showing a brief overview of a scanning electron microscope according to the present invention.

1: electron source (electron gun)
2: electron beam
3: lens system
4: sample
5: secondary electron
6: secondary electron detection system
7: control system
8: xyz stage 9: image display device
10: design data managing unit

DESCRIPTION OF THE PREFERRED EMBODIMENT

A brief overview of a scanning electron microscope according to the present invention is described with reference to FIG. 1. The scanning electron microscope of the present invention has a length measuring function of measuring a shape and a dimension of a pattern formed on a wafer used for manufacturing a semiconductor integrated circuit, or on a photomask, and this is also referred to as a "length measuring SEM".

The scanning electron microscope of this embodiment has an electron source (electron gun) 1, a lens system 3, a secondary electron detection system 6, and an x-y-z stage 8. A sample 4 is movable in a three-dimensional direction or in an x-y two-dimensional direction by the x-y-z stage 8. The scanning electron microscope of this embodiment further has a control system 7, an image display device 9, and a deign data managing unit 10. The control system 7 has an image arithmetic control function, and also controls the electron source 1, the lens system 3, the secondary electron detection system 6, the x-y-z stage 8, and the image display device 9.

An electron beam 2 from the electron source (electron gun) 1 is focused by the lens system 3, two-dimensionally scanned (in the x-y direction) by a scanning coil not shown, and is irradiated on the sample 4. A secondary electron 5 from a surface of the sample 4 is detected by the secondary electron detection system 6, and is supplied to the control system 7 (control processor) as image data. The image data is amplified by a signal amplifier in the control system 7, transferred to an image memory, and is displayed by the image display device 9 as a sample image.

A secondary electron detector may be the one for detecting the secondary electron and a reflected electron, or the one for detecting light and an X-ray. An input device not shown is provided in the control system 7, and it is possible to specify capturing conditions of the image (scanning speed and image accumulation number) and a viewing area correcting method, and to specify output and saving of the image.

The control system 7 or a separately provided computer generates an address signal corresponding to a memory location of an image memory, and converts the same to an analog signal to supply to the scanning coil not shown. In this manner, an address of the image memory and the address of a deflection signal for scanning the electron beam correspond to each other, so that a two-dimensional image of a deflection scanning area of the electron beam by the scanning coil is recorded in the image memory.

For example, when the image memory has 512×512 pixels, the address signal in an x-direction is a digital signal repeating from 0 to 512, and the address signal in a y-direction is the digital signal repeating from 0 to 512, which is incremented by one when the address signal in the x-direction reaches from 0 to 512. The digital signals are converted to the analog signals and are supplied to the scanning coil.

The image signal recorded in the image memory may be sequentially read out in time-series by a read address generating circuit in synchronization with a read clock. In this manner, the image signal, which is read out so as to correspond to the address, is analog converted to be an intensity modulation signal of the image display device 9.

The design data managing unit 10 has a function of converting design data of a pattern of the semiconductor wafer or the photomask, inputted by the input device not shown, and creating a recipe. The recipe is data necessary for controlling the scanning electron microscope, and conditions (such as a measurement point and an optical condition of the scanning electron microscope) when a plurality of points on the semiconductor wafer or on the photomask being observed are described therein. The scanning electron microscope measures and observes according to contents of the recipe. The design data managing unit 10 has a function of rewriting the recipe based on the signal transmitted from the control system 7. In the scanning electron microscope shown in FIG. 1, the design data managing unit 10 is provided as a component separate from the control system 7. However, the design data managing unit 10 may be provided integral with the control system 7 or as the component thereof.

The scanning electron microscope of this embodiment has a function of forming a line profile from the secondary electron, the reflected electron, or the like detected by the secondary electron detection system 6. The line profile is formed based on a detected amount of the electron detected by the secondary electron detection system 6, intensity information of the sample image, or the like when a primary electron beam being scanned one-dimensionally or two-dimensionally. The line profile is used to measure a dimension of the pattern formed on the semiconductor wafer or the pattern on the photomask.

In the scanning electron microscope shown in FIG. 1, the control system 7 is provided integrally with the scanning electron microscope or as the component thereof. However, the control system 7 may be configured as a control processor provided separately from a body of the scanning electron microscope. In this case, transmission media and an input/output terminal for inputting and outputting the signal transmitted through the transmission media are provided between the control processor and the scanning electron microscope. A detection signal detected by a secondary signal detector is transmitted to the control processor through the transmission media. In addition, the signal is transmitted from the control processor to a lens and a deflector of the scanning electron microscope through the transmission media.

It is also possible to configure such that a program for performing a process to be described below is registered into a memory media and a necessary instruction signal is supplied from the control processor to the scanning electron microscope to execute the program. The process to be described below is performed by the program loadable into the scanning electron microscope provided with an image processor or by a program product. Meanwhile, although the scanning electron microscope is described herein, the present invention is also applicable to a charged particle radiation apparatus.

The scanning electron microscope of this embodiment sets the wafer used for manufacturing a semiconductor integrated circuit or the photomask, as the sample 4. In the following description, the sample 4 is the photomask used for manufacturing a semiconductor integrated circuit, which is formed by photolithography. To manufacture the photomask, first, a shaded film composed of thin-film chromium or molybdenum silicide is formed on a quartz substrate, and a resist is applied onto the shaded film. Next, a resist pattern based on CAD data is formed by an electron beam drawing device. Then, a shaded film pattern is formed on the substrate by developing and etching. Although a dimension is measured principally for the shaded film pattern, this might be measured for the resist pattern after development.

The photomask pattern is inspected by the scanned image of the photomask pattern. In this inspection, the scanned image of the photomask and a standard pattern of the photomask are compared to each other. The CAD data used for generating the photomask pattern may be used as the standard pattern of the photomask. On the assumption that a conversion magnification between the wafer pattern and the mask pattern is fourfold, the CAD data of the photomask is obtained by quadrupling an original wafer pattern data (CAD data). Such a change in the magnification of the data and a change in the position of the pattern data associated with the same may be easily executed by an Affin conversion or the like. Hereinafter, the CAD data of the photomask is simply referred to as the "CAD data".

The photomask pattern may be OPC processed as well as the wafer pattern. In this case, the CAD data of the photomask is obtained by quadrupling an OPC processed wafer pattern data (CAD data). The OPC processed CAD data of the photomask thus obtained is simply referred to as "OPC processed CAD data".

According to the present invention, a width dimension of the photomask pattern is measured by the scanned image of the photomask pattern formed by the photolithography. When the width dimension of the photomask pattern being measured, it is required to set a measurement area. According to the present invention, the standard pattern of the photomask is used when the measurement area being set. As described below, the standard pattern of the photomask is the "CAD data" or the "OPC processed CAD data".

Figure 2:
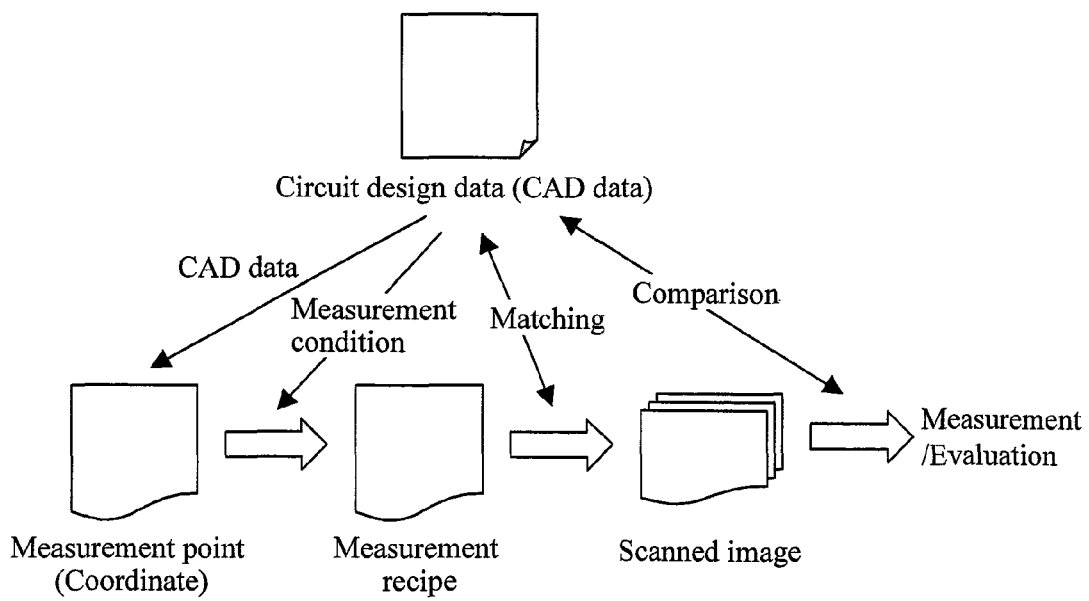
FIG. 2 is a view illustrating a brief overview of a measurement method of a pattern according to the present invention.

A brief overview of a measurement method of the pattern according to the present invention is described with reference to FIG. 2. The sample is the photomask. First, the CAD data corresponding to the measurement point on the photomask is acquired and the measurement condition or the like is set. Next, the recipe for measuring the measurement point by the scanning electron microscope is created. Then, the scanned image of the measurement point on the mask is obtained according to the recipe. Next, the image is compared to the CAD data and the measurement area is set. Further, the width dimension of the pattern is measured by using a contour in the measurement area and is evaluated. In a series of the processes, positioning referred to as addressing for adjusting the measurement point, and operation such as focusing for focusing the electron beam on the pattern are required. The processes may be performed by using, for example, the method disclosed in JP-A No. 2006-234588.

The measurement area is set so as to include a given measurement point. In the measurement method of the pattern according to the present invention, it is measured so as to avoid roundness of a corner portion of the pattern in the measurement area. This is described in detail below.

Figure 3:
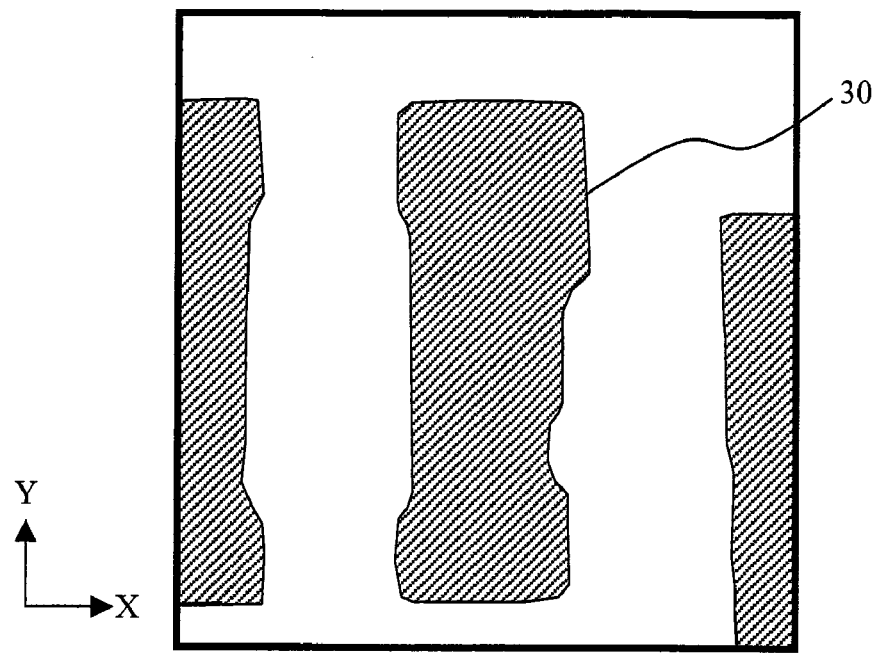
FIG. 3 is a view showing an example of a scanned image of a photomask pattern obtained by the scanning electron microscope.

FIG. 3 is a view showing an example of the scanned image of a photomask pattern 30 obtained using the scanning electron microscope. The magnifying power thereof is 70,000 fold. An image display area of the image display device is 130 mm square. Therefore, the scanned image shows the image of the area of substantially 1.86 μm (micron meter) square. Hereinafter, in the scanned image, a horizontal direction is the x-direction and a vertical direction is the y-direction.

The photomask pattern 30 has the roundness formed on the corner portion. The roundness is due to a manufacturing process such as drawing, resistor etching in a process for manufacturing a mask. Therefore, it is not possible to obtain the pattern identical to the CAD data of the photomask.

Figure 4:
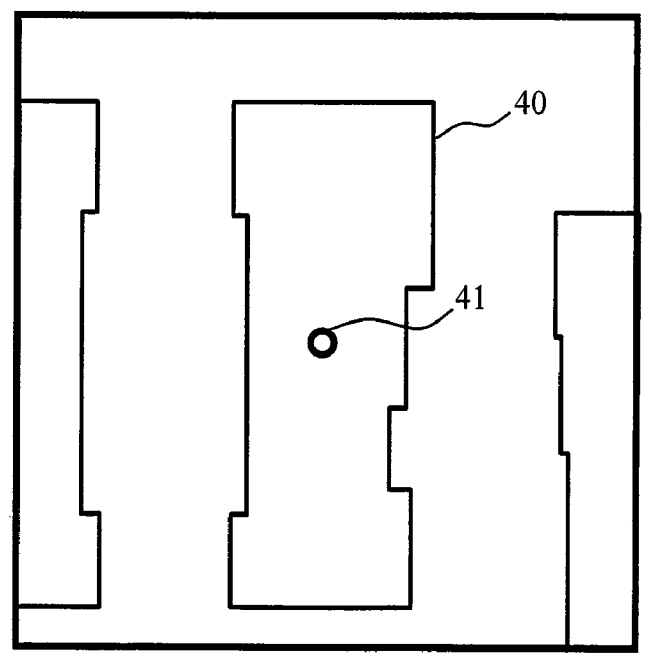
FIG. 4 is a view showing an example of CAD data of the photomask.

FIG. 4 is a view showing CAD data 40 of the photomask used for generating the photomask pattern in FIG. 3. A circle on a center portion represents a measurement point 41. The measurement point 41 is given in advance in the CAD data. The CAD data is created in a format such as GDSII or OASIS. In the formats, the pattern is basically defined as a polygonal sequence of dots. A shape of the pattern is defined by connecting the sequence of dots by use of straight lines. Hereinafter, it is assumed that the CAD data is created in the GDSII format.

Generally, the pattern of the photomask is basically rectangular. The pattern of the photomask is formed by superposing rectangles. An outline of the pattern is obtained by eliminating an overlapping portion of the pattern. A process for eliminating the overlapping portion of the pattern is easy and is known by one skilled in the art, so that the description thereof will not be repeated here.

Figure 5:
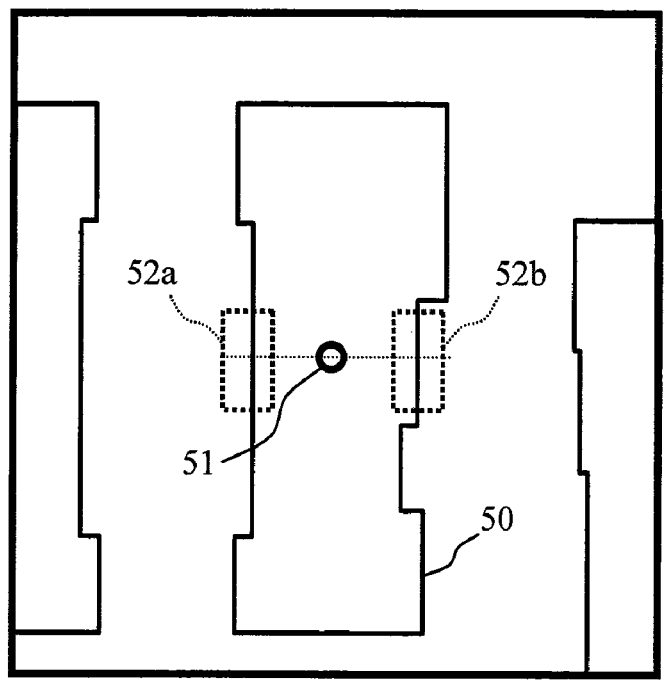
FIG. 5 is a view showing an example of CAD data of the photomask.

The conventional pattern measurement method is described with reference to FIGS. 5 and 6. Herein, an example is described in which the CAD data is the standard data and the width dimension of the pattern is measured. FIG. 5 is a view showing CAD data 50 of the photomask. As shown, measurement areas 52a and 52b are set. The measurement areas 52a and 52b are generally referred to as cursor boxes. In this example, a dimension in the y-direction of the measurement areas 52a and 52b is substantially 600 nm.

Generally, the measurement areas 52a and 52b are inputted in advance in the CAD data as additional information. Therefore, the measurement point 51 and the measurement areas 52a and 52b are automatically displayed. However, it is also possible that an operator sets the measurement areas 52a and 52b based on the measurement point 51 while watching the scanned image. In this example, two measurement areas 52a and 52b are set. That is to say, the measurement areas 52b and 52a are set on right and left outlines of the pattern, respectively. However, one measurement area including both the right and left outlines of the pattern may be set.

Figure 6:
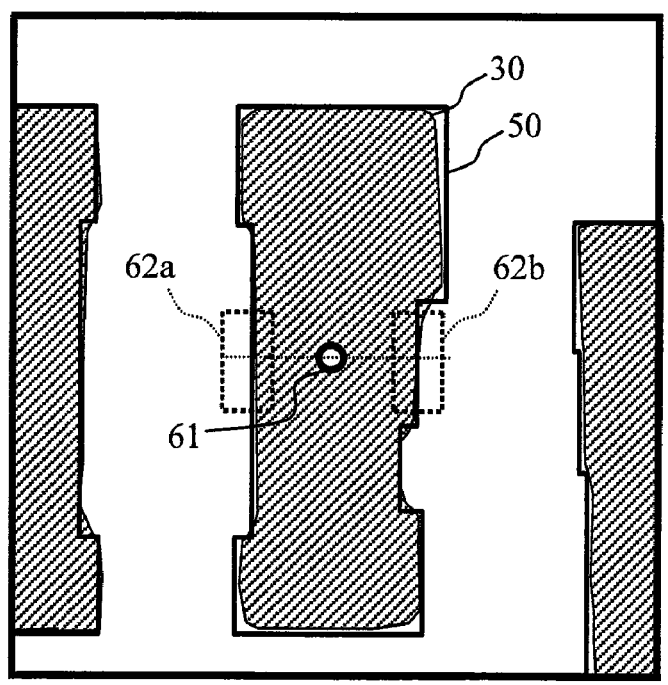
FIG. 6 is a view showing an example of displaying the CAD data of the photomask so as to be superimposed on the scanned image of the photomask pattern.

FIG. 6 is a view showing the CAD data 50 of the photomask in FIG. 5 so as to be superimposed on the scanned image of the photomask pattern 30 in FIG. 3. The width dimension of the pattern is obtained by measuring a distance between the contour of the pattern included in the one measurement area 62a and the contour of the pattern included in the other measurement area 62b. In the measurement area 62a on the left side, the contour of the pattern is a straight line. The right measurement area 62b on the right side includes the roundness of the corner portion of the pattern. Therefore, in the measurement area 62b on the right side, the contour of the pattern is bent in an upper portion. In this example, a design value of the width dimension of the pattern is 500 nm. When measuring the width dimension of the pattern for the two measurement areas 62a and 62b, this was 506 nm, for example. At that time, assuming that a tolerance of the width dimension of the pattern is plus or minus 4 nm, this pattern is defective and is judged to be off-specification.

The measurement of the width dimension of the pattern is quantitative comparative evaluation between the dimension of an actually formed photomask pattern and the CAD data of the photomask. Therefore, when a portion including the roundness of the corner portion is included in the measurement area, a correct measurement is not obtained. Then, the measurement area may be set by detecting the corner portion of the pattern and excluding a certain area around the corner portion.

Figure 7:
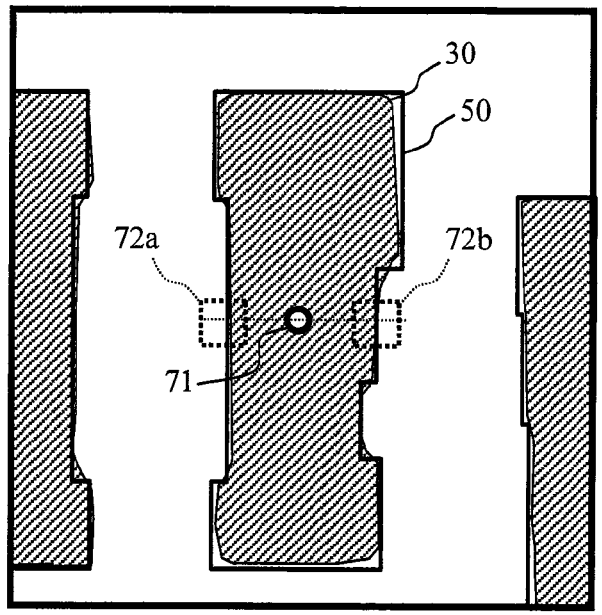
FIG. 7 is a view showing an example of displaying the CAD data of the photomask so as to be superimposed on the scanned image of the photomask pattern in order to illustrate the present invention.

A first embodiment of the pattern measurement method of the present invention is described with reference to FIGS. 7 and 8. FIG. 7 is a view showing the CAD data 50 of the photomask in FIG. 5 so as to be superimposed on the scanned image of the photomask pattern 30 in FIG. 3, just as in FIG. 6. However, in this embodiment, the dimension in the y-direction of the measurement areas 72a and 72b is substantially 300 nm. That is to say, the dimension in the y-direction of the measurement areas 72a and 72b of this embodiment is half the dimension in the y-direction of the measurement areas 62a and 62b shown in FIG. 6. Meanwhile, the dimension in the x-direction of the measurement areas 72a and 72b of this embodiment may be identical to the dimension in the x-direction of the measurement areas 62a and 62b shown in FIG. 6. In this manner, in this embodiment, the roundness of the corner portion of the pattern is never included in the measurement area 72b on the right side by making the dimension in the y-direction of the measurement areas 72a and 72b smaller. That is to say, in the measurement areas 72b and 72a on the right and left sides, the contours of the pattern are substantially straight lines. Therefore, the width dimension of the pattern may be correctly measured. In this embodiment, when a width dimension of the pattern was measured, it was 503 nm, for example. This pattern is normal and is judged to be within the specification.

A process for setting the measurement area of the first embodiment of the pattern measurement method according to the present invention, is especially described with reference to FIG. 8. Meanwhile, in order to facilitate understanding, the pattern of the photomask of a measurement object is shown on the right side or the left side of the process. Predetermined conditions are set at a step S101. Herein, the conditions to be set are the CAD data of the photomask, the measurement point, that a measuring direction is in the x-direction, and that the width dimension of the pattern is 500 nm, or the like.

A line segment of the pattern of the measurement object is decided using the CAD data of the photomask at a step S102. First, two points spaced away from the measurement point in positive and negative x-directions by 250 nm are calculated. Next, outlines including their respective two points are decided. When there is no outline including their respective two points, the outlines the closest to their respective two points are decided. They become line segment data of the pattern of the measurement object. As shown in FIG. 5, the line segments are straight lines extending in the y-direction among the polygonal outlines. The pattern is not necessarily symmetric, so that lengths of the right and left line segments are not necessarily the same. Hereinafter, it is described on the assumption that the lengths of the right and left line segments are different.

As described above, the pattern data of the photomask is a polygon formed of sequences of dots, so that it is easy to judge on which sequence of dots the two points and the outlines are. However, when a plurality of patterns is close to one another, it requires an amount of time to judge due to the increased number of line segments to be judged. However, since the measurement points are known, it is only necessary to search the outlines of the pattern in the vicinity. It is easy to obtain the two points from the measurement point and to decide the two line segments of the pattern the closest to their respective two points.

The line segments of a certain length from both end points of the two line segments are excluded at a step S103. The length to be eliminated is determined in advance, and for example, this may be set at the step S101. In this manner, when the same length is eliminated from the two line segments, the lengths of the two line segments become short, however, the two line segments are different from each other in length. In this embodiment, the length to be eliminated is 150 nm. This is because it is judged that the roundness of the corner portion of the pattern affects the area within 150 nm from the end points of the two line segments.

The measurement area is set at a step S104. The measurement areas of the same dimension are set with respect to the two line segments. First, the lengths of the right and left line segments are compared. The positions of the two end points on upper portions of the right and left line segments are compared and the end point closer to the measurement point is picked out. Similarly, the positions of the two end points on lower portions are compared and the end point closer to the measurement point is picked out. Next, two lines passing through their respective end points thus picked out and extending in the x-direction are drawn. By the two lines, an upper side and a lower side of the measurement area are formed.

Next, right and left sides of the measurement area are formed. A dimension of the measurement area in the x-direction is determined in advance. Therefore, the right and left sides of the measurement area are easily formed. The dimension of the measurement area in the x-direction may be set in advance, for example, at the step S101. At that time, it is only necessary to confirm that the two line segments do not enter one measurement area, or that the two line segments are spaced apart from the measurement area by a predetermined distance. In this manner, the same measurement areas are set with respect to the two line segments. Such a confirmation process may be performed just as algorithm shown in FIG. 8. As described above, one measurement area including the right and left outlines of the pattern may be set in place of setting the two measurement areas.

In a scan method in the scanning electron microscope, the address signal is increased from left to right with respect to the x-direction, and when this reaches the maximum, the address signal is incremented by one in the y-direction to scan again in the x-direction. Therefore, it is required that the widths in the y-direction of the right and left measurement areas are identical.

The decided measurement areas are stored in the design data managing unit 10 in the scanning electron microscope at a step S105.

A second embodiment of the pattern measurement method according to the present invention is described with reference to FIGS. 9 to 12. Although the measurement areas are decided from both the CAD data of the photomask and the measurement point in the first embodiment shown in FIGS. 7 and 8, in this embodiment the measurement areas are decided using both the CAD data of the photomask and the scanned image of the actually obtained pattern of the photomask.

Figure 9:
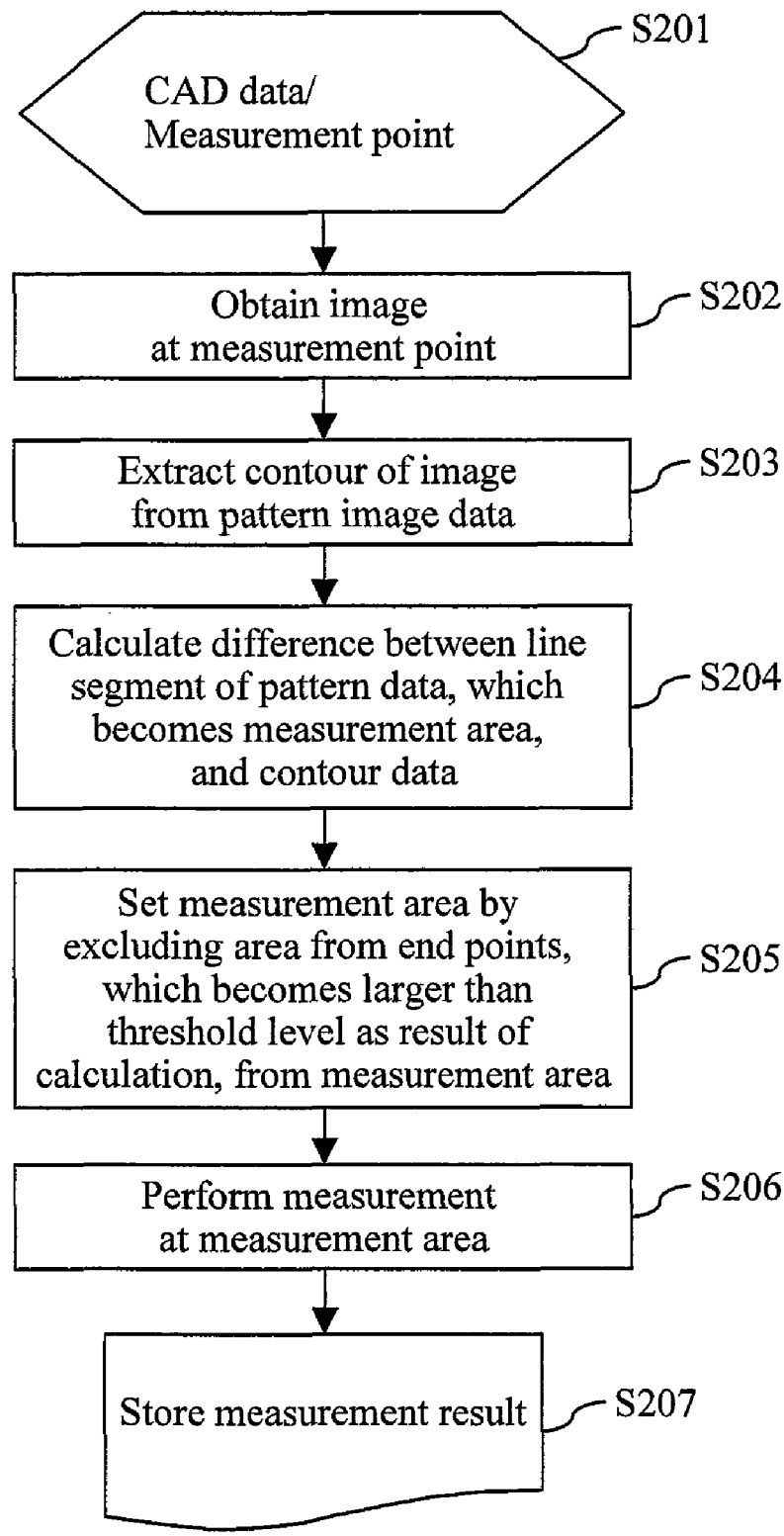
FIG. 9 is a view illustrating a second embodiment of the pattern measurement method according to the present invention.

This is described with respect to FIG. 9. Predetermined conditions are set at a step S201. The conditions to be set herein are the CAD data of the photomask and the measurement point. At a step S202, in the area including the measurement point, the scanned image of the pattern of the photomask is obtained. At a step S203, the contour of the pattern of the photomask is extracted from the scanned image. The contour is extracted from a result of a calculation of an intensity distribution of the image data. A process for extracting contour may be performed by the same method and standard as the algorithm of the dimension measurement. The contour is made GDS data, that is to say, made a sequence of dots, just as the CAD data.

At a step S204, in the area including and in the vicinity of the measurement point, the contour and the CAD data of the photomask are compared to each other. First, two line segments of the CAD pattern are decided by the method similar to the method of deciding the line segments of the pattern of the measurement object at the step S102 in FIG. 8. Differences between the two line segments and the contours the closest to the two line segments are calculated. Both the contour and the CAD data of the photomask are sequences of dots of the GDS data. Therefore, the differences are obtained as the GDS data.

The measurement areas are set at a step S205. Among the contours, the area of which difference is large or the area in which variation in the difference value is large may be judged to be the portion of the roundness of the corner portion. For example, the area in which the difference value or a variation amount of the difference value is larger than a predetermined threshold level is judged to be the roundness of the corner portion. In this manner, the area judged to be the roundness of the corner portion is excluded from the two line segments of the CAD pattern. Next, the measurement areas are set from the two line segments. An example of the method of setting the measurement areas is described hereinafter with respect to FIGS. 10 and 11. As described above, the right and left identical measurement areas are set.

At a step S206, in the measurement areas, the dimension of the pattern width of the measurement object is measured from the scanned image of the pattern of the photomask. At step S207, a result of the measurement is saved.

Figure 10:
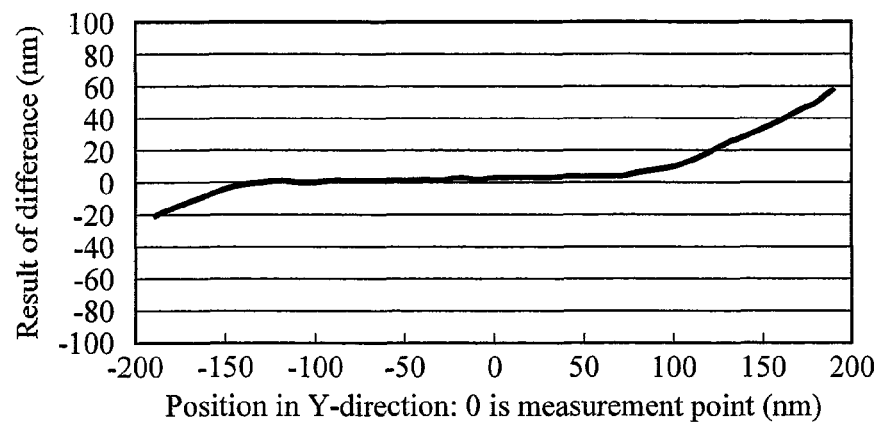
FIG. 10 is a view showing a calculation result of a difference in a contour on the right side of the pattern.

FIG. 10 is a view showing a calculation result of the difference in the contour on the right side of the pattern. Meanwhile, it is represented as (difference)=(sequence of dots of data of the contour GDS)−(sequences of dots of CAD data). A longitudinal axis represents the difference (nm), a transversal axis represents a position in the y-direction (longitudinal direction of the image), in which the measurement point is 0. According to this embodiment, when the position in the y-direction becomes higher than near +100, the difference value increases. This indicates an effect of the roundness of the corner portion.

Figure 11:
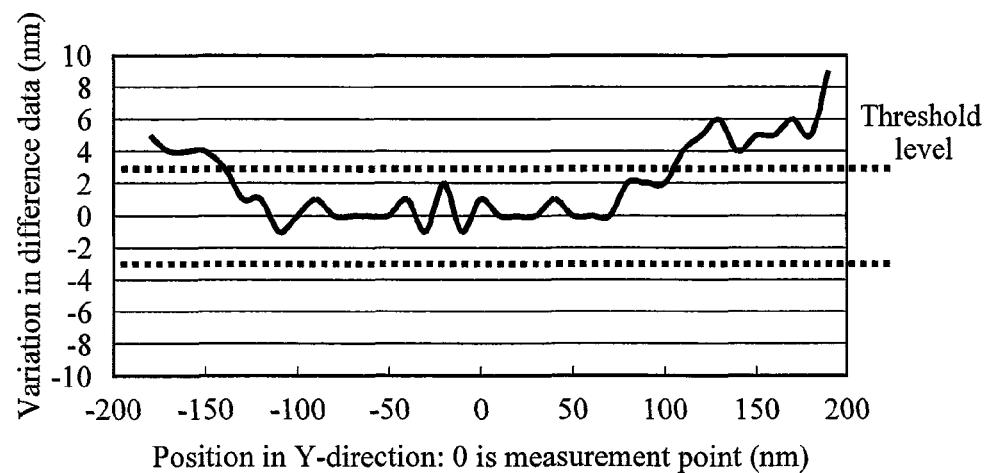
FIG. 11 is a view showing a calculation result of variation in the difference value.

FIG. 11 is a view showing a result of calculation of the variation in the difference value from the difference data in FIG. 10. In the difference data in FIG. 10, a variation amount between the adjacent difference values was used as the variation amount. In this embodiment, the threshold level is set to ±3.5 nm. According to this embodiment, when the position in the y-direction becomes larger than near +100, the variation amount becomes larger than the threshold level. From the result in FIGS. 10 and 11, an area from −130 to +100 nm in the y-direction (longitudinal direction in the image) may be set as the measurement area.

Figure 12:
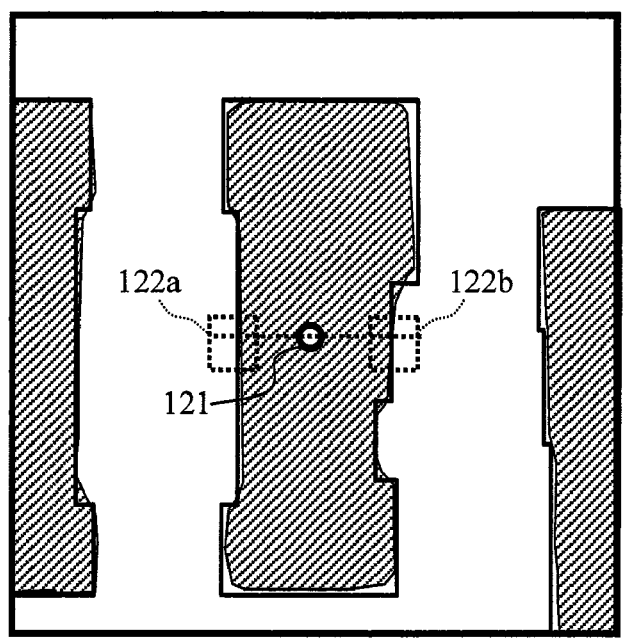
FIG. 12 is a view showing an example of displaying the CAD data so as to be superimposed on the actually obtained scanned image of the photomask pattern.

FIG. 12 is a view showing both the CAD data and the scanned image of the actually obtained pattern of the photomask so as to be superimposed on each other. The measurement areas 122a and 122b are set according to the second embodiment of the pattern measurement method of the present invention. As compared to the measurement areas 72a and 72b shown in FIG. 7, in the measurement areas 122a and 122b in this embodiment, the area of an upper side (positive y-direction) from the measurement point 121 becomes smaller. That is to say, a distance from the measurement point 121 to the upper side is smaller than the distance to the lower side. This is because the difference value in the area in the upper side from the measurement point 121 is large, so that the line segment in this portion is excluded.

According to this embodiment, by using both the CAD data of the photomask and the contour data extracted from the scanned image of the pattern, it is possible to automatically set an adequate measurement area even for a complicated photomask pattern. Therefore, it is possible to correctly measure the dimension of the pattern width.

According to this embodiment, in the portion, which is the roundness of the corner portion, the line segment of the CAD data of the photomask is largely separated from the contour extracted from the image pattern, or the variation in the difference value of both is large. Therefore, it is possible to eliminate the effect of the roundness of the corner portion, by excluding the area in which the difference between the line segment of the CAD data of the photomask and the contour extracted from the scanned image is larger than the threshold level set in advance, from the measurement area.

In the embodiment, the pattern of the photomask may be the OPC processed one or the one without the OPC processing. When the OPC processed one is used, the OPC processed CAD data is used as the CAD data of the photomask.

Figure 8:
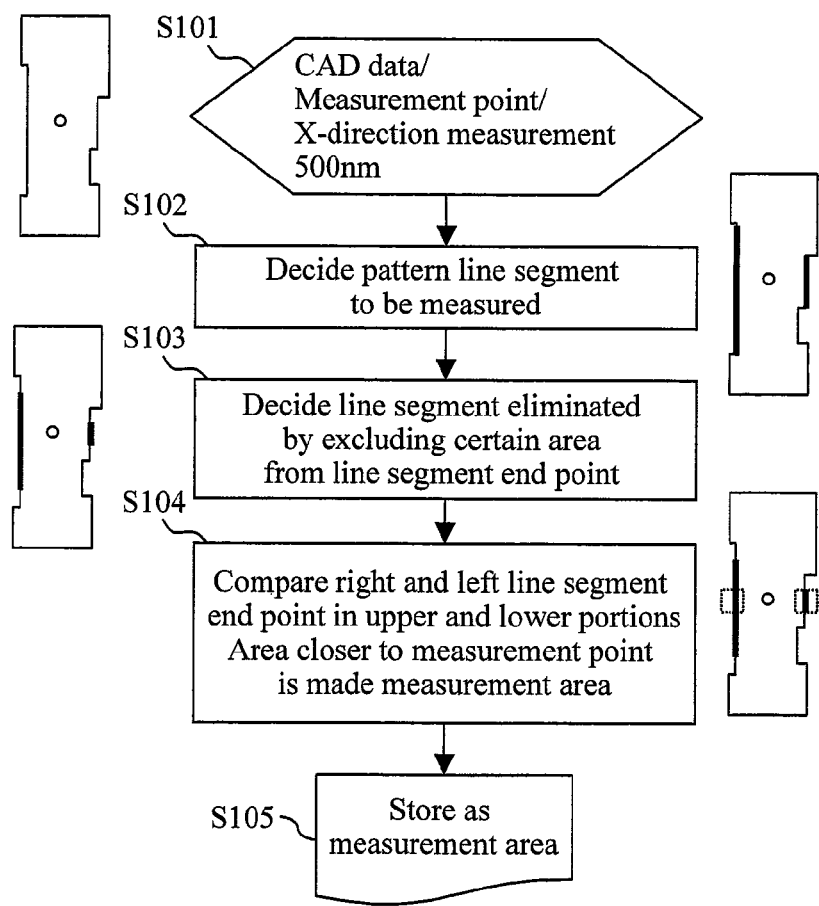
FIG. 8 is a view especially illustrating a process to set the measurement area out of the pattern measurement method according to the present invention.

In the first embodiment shown in FIGS. 7 and 8 and the second embodiment shown in FIGS. 9 to 12, the width dimension of the pattern of the photomask actually formed is measured from the scanned image. In a third embodiment of the pattern measurement method according to the present invention to be described below, the width dimension of the OPC processed photomask pattern is measured. Generally, the pattern of the photomask changed by the OPC technology is referred to as an OPC pattern, and in a mask manufacturing process, the dimension of the OPC pattern is often measured. In order to judge whether the pattern on the wafer is correct or not, it is required to inspect an OPC processed photomask CAD data. In this embodiment, the OPC processed photomask CAD data is obtained by quadrupling the original wafer pattern data (CAD data). Hereinafter, the OPC processed photomask CAD data is simply referred to as the "OPC processed CAD data".

Figure 13:
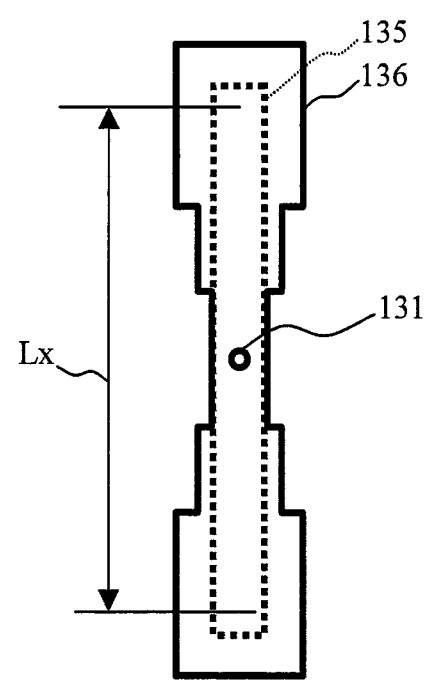
FIG. 13 is a view for illustrating a third embodiment of the pattern measurement method according to the present invention.

The third embodiment of the pattern measurement method according to the present invention is described with reference to FIG. 13. FIG. 13 is a view showing the pattern 135 of the photomask without the OPC processing so as to be superimposed on the OPC processed photomask pattern 136. Both of them are the CAD data. The CAD data of the OPC processed photomask is obtained by quadrupling the CAD data of the OPC processed original wafer pattern. The CAD data of the photomask without the OPC processing is obtained by quadrupling the CAD data of the original wafer pattern without the OPC processing.

In this embodiment, the width dimension of the original wafer pattern without the OPC processing is 45 nm, and the width dimension of the pattern 135 of the photomask without the OPC processing indicated by a broken line is 45×4=180 nm. The pattern 135 of the photomask without the OPC processing is a rectangle having a constant width dimension, however, the OPC processed photomask pattern 136 is the polygon of which width dimension is changed in a step-like manner. That is to say, the width dimension of the OPC processed photomask pattern 136 becomes larger as it is closer to both ends. To change the width dimension of the pattern in this manner is referred to as optical proximity correction (OPC).

Herein, an optical proximity effect and the optical proximity correction (OPC) are simply described. When the width dimension of the pattern becomes minute, it becomes difficult to obtain the pattern identical to the pattern (CAD data) of the photomask. For example, when forming the pattern by the photolithography technique using the pattern 135 of the photomask without the OPC processing, the pattern having the same shape as the pattern 135 may not be obtained. The pattern actually obtained is in the shape in which the corner portion is rounded and the width dimension is narrowed at the tip ends. This is due to the optical proximity effect. The effect of the optical proximity effect is larger at the tip ends of the pattern. Therefore, by using the OPC processed photomask pattern 136, the pattern having the shape substantially similar to that of the pattern 135 of which corner portion is sharp may be obtained.

In the vicinity of the measurement point 131, the width dimension of the OPC processed photomask pattern 136 is identical to the width dimension of the pattern 135 of the photomask without the OPC processing. This is due to the small optical proximity effect in the central portion of the pattern.

The shape of the OPC processed photomask pattern 136 depends on the shape of the original wafer pattern without the OPC processing. When the original wafer pattern without the OPC processing is symmetrical as in this embodiment, the shape of the OPC processed photomask pattern 136 is symmetrical.

In FIG. 13, a standard dimension Lx is set. The standard dimension Lx indicates an area in which the measurement area may be set. The standard dimension Lx is set based on the pattern 135 of the photomask without the OPC processing. When the pattern is formed by the photolithography technique using the OPC processed photomask pattern 136, the pattern having the shape substantially identical to that of the pattern 135 of the photomask without the OPC processing is obtained, but, actually, the tip end thereof is slightly rounded. Therefore, the tip end is excluded from the area on which the measurement area is set. Therefore, in this embodiment, the standard dimension Lx is set to a value slightly smaller than the dimension in the x-direction of the pattern 135 of the photomask without the OPC processing.

Figure 14:
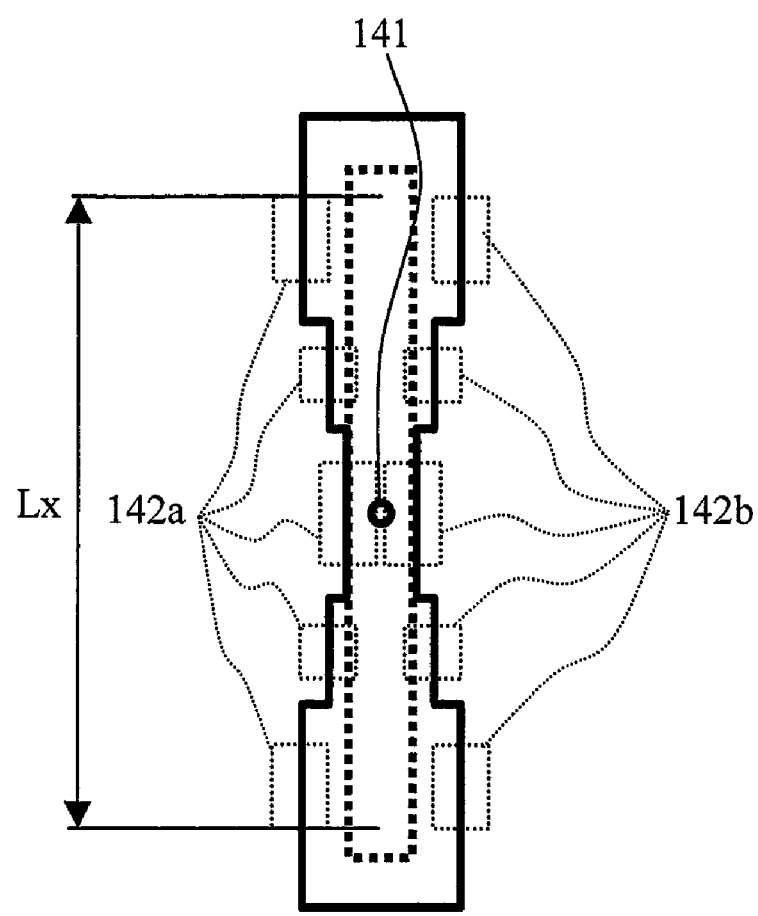
FIG. 14 is a view showing a state in which the measurement area is set on the OPC processed photomask pattern.

FIG. 14 is a view showing a state in which the measurement areas 142a and 142b are set on the OPC processed photomask pattern 136. The measurement areas 142a and 142b are set in the area of the standard dimension Lx. In this embodiment, the measurement areas 142a and 142b are set for each of the line segments having different width dimensions among the OPC processed photomask pattern 136. The right and left measurement areas 142b and 142a are identical in dimension and in shape.

The process for setting the measurement areas 142a and 142b on the OPC processed photomask pattern 136 is similar to that in the first or second embodiment. That is to say, a line segment of a predetermined length is excluded from the outlines of the OPC processed photomask pattern 136 so as not to be affected by the corner portion. The measurement area is set on the line segments thus obtained.

In this manner, in this embodiment, the width dimension of the OPC processed photomask pattern 136 is measured in a plurality of measurement areas. Therefore, in this embodiment, it is possible to correctly determine quality of the OPC processed photomask pattern 136.

Meanwhile, although not shown in FIG. 14, it is possible to further display the scanned image of the actually formed wafer pattern so as to be superimposed. Thereby, it is possible to compare the actually formed wafer pattern and the pattern 135 of the photomask without the OPC processing. In the area in which both conform to each other, it is possible to judge that the width dimension of the OPC processed photomask pattern 136 is adequate.

In the first, second and third embodiments, the two measurement areas are set. However, it is possible to set one horizontally long measurement area.

In this embodiment, only by specifying the measurement point, the measurement area is automatically set on the OPC processed photomask pattern. Therefore, it becomes easy to evaluate the width dimension of the OPC processed photomask pattern. Also, according to the method of this embodiment, by setting the measurement point by the scanning electron microscope and obtaining the scanned image, then, the setting of the measurement area and the measurement of dimension in the measurement area may be performed off-line. Therefore, an occupation time of the scanning electron microscope is shortened and a throughput is improved accordingly.

According to the present invention, it becomes possible to automatically measure the dimension of the pattern by eliminating the effect of the corner portion of the pattern. Also, in the OPC pattern having a complicated shape, the quantitative dimension evaluation of the pattern becomes possible. Further, the CAD data of the wafer pattern is used as the standard data when measuring the dimension of the OPC pattern of the photomask. Thereby, it becomes possible to compare the wafer pattern and the OPC pattern of the photomask. Therefore, accuracy in the evaluation of the pattern in the OPC pattern of the photomask is improved. Further, when the dimension of the wafer pattern is abnormal, its correlation with the OPC pattern of the photomask may be quantitatively judged.

Further, according to the measurement method of the present invention, the measurement area is set by using the CAD data. Therefore, in a measuring device such as the scanning electron microscope, the image may be obtained based on the measurement point. Then, the image is transmitted to the measuring device or a different evaluation device, the measurement area is set using the CAD data, and the dimension of the pattern is measured. Therefore, it is not required to set the measurement area in the measuring device, so that the measurement time may be shortened. Further, the process time may be improved. Also, it is easy to evaluate again the once obtained image, so that the processing time may be comprehensively reduced.

Although the embodiment of the present invention has been described as above, the present invention is not limited to the embodiment, and one skilled in the art may easily comprehend that various change is possible in the scope of the invention encompassed by claims.

What is claim is:

1. A pattern measurement method for measuring a dimension of a predetermined pattern on a sample from a scanned image by a scanning electron microscope, comprising steps of:
   obtaining a standard pattern corresponding to the predetermined pattern and a measurement point specified in advance;
   setting a measurement area so that it includes two straight line segments on both sides of the measurement point out of outlines of the standard pattern; and
   measuring a dimension between two contours of a scanned image of the predetermined pattern in the measurement area by superposing the measurement area on the scanned image of the predetermined pattern,
   wherein the step of setting the measurement area sets the measurement area so that it does not include portions near corner portions connected to the two line segments.

2. The pattern measurement method according to claim 1, wherein the step of setting the measurement area includes steps of:
   selecting the two straight line segments on both sides of the measurement point and the closest to the measurement point among the outlines of the standard pattern;
   detecting end points of both ends of each of the two line segments and cutting a line segment of a predetermined length from the end points to shorten;
   selecting two end points the closest to the measurement point among the end points of both ends of each of the shortened two line segments; and
   setting two sides of the measurement areas based on the selected two end points.

3. The pattern measurement method according to claim 2, wherein the steps of selecting the two line segments includes steps of calculating two points spaced away from the measurement point by a predetermined distance, and detecting the line segments including their respective two points or line segments the closest to their respective two points.

4. The pattern measurement method according to claim 1, wherein the step of setting the measurement area includes steps of:
selecting straight two line segments on both sides of the measurement point and the closest to the measurement point among the outlines of the standard pattern;
detecting two contours of the scanned image of the predetermined pattern corresponding to the selected two line segments;
calculating a distance between the two line segments of the standard pattern and the two contours of the scanned image of the predetermined pattern corresponding to the two line segments;
detecting an area the distance or a variation amount of the distance of which is larger than a predetermined threshold level;
eliminating a line segment included in the detected area from the two line segments of the standard pattern to shorten;
selecting two end points the closest to the measurement point among the end points of both ends of each of the shortened two line segments; and
setting two sides of the measurement areas based on the selected two end points.

5. The pattern measurement method according to claim 1, wherein the predetermined pattern on the sample is a pattern of a photomask used in semiconductor manufacturing, and the standard pattern is CAD data of the pattern of the photomask.

6. The pattern measurement method according to claim 5, wherein the CAD data of the pattern of the photomask is OPC processed CAD data.

7. The pattern measurement method according to claim 1, wherein the measurement area is provided on each of the two line segments.

8. The pattern measurement method according to claim 1, wherein only one measurement area is provided so as to include the two line segments.

9. A pattern measurement method for measuring a dimension of a pattern of a photomask from a scanned image by a scanning electron microscope, comprising steps of:
obtaining both data of an OPC processed photomask pattern including a pattern of which width dimension changes in a step-like fashion, and a measurement point set in advance;
setting a measurement area so as to include straight two line segments on both sides of the measurement point among outlines of the pattern of the photomask; and
measuring a dimension between two line segments of the pattern of the photomask in the measurement area,
wherein the step of setting the measurement areas includes steps of:
selecting a group of the two line segments having different width dimensions on both sides of the measurement point among the outlines of the pattern of the photomask, and setting a measurement area for each of the group of the two line segments.

10. The pattern measurement method according to claim 9, wherein the step of setting the measurement area includes steps of:
obtaining a standard pattern corresponding to the OPC processed photomask pattern; and
setting a standard dimension with respect to the standard pattern, and the step of selecting the group of the two line segments selects the group of the two line segments in an area of the standard dimension.

11. The pattern measurement method according to claim 10, wherein the standard pattern is obtained by magnifying data of the pattern of the photomask without the OPC processing at a predetermined magnification.

12. The pattern measurement method according to claim 9, wherein data of the OPC processed photomask pattern is OPC processed CAD data.

13. A pattern measurement system for measuring a dimension of a predetermined pattern on a sample from a scanned image by a scanning electron microscope, comprising:
a design data managing unit that stores both a standard pattern corresponding to the predetermined pattern and a measurement point specified in advance; and
a control device that sets a measurement area so as to include two straight line segments on both sides of the measurement point among outlines of the standard pattern, superposes the measurement area on the scanned image of the predetermined pattern, and measures a dimension between two contours of the scanned image of the predetermined pattern in the measurement area,
wherein the control device sets the measurement area so that it does not include portions near corner portions connected to the two line segments, and saves the measurement area in the design data managing unit.

14. The pattern measurement system according to claim 13, wherein a predetermined pattern on the sample is a pattern of the photomask used in semiconductor manufacturing, and the standard pattern is CAD data of the pattern of the photomask.

15. A pattern measurement system for measuring a dimension of a pattern of a photomask from a scanned image by a scanning electron microscope, comprising:
a design data managing unit for storing data of an OPC processed pattern photomask including a pattern of which width dimension changes in a step-like fashion, and a measurement point set in advance; and
a control device for setting a measurement area so that it includes two straight line segments on both sides of the measurement point among outlines of the pattern of the photomask to measure a dimension between two line segments of the pattern of the photomask in the measurement area,
wherein the control device selects a group of two line segments having different width dimensions on both sides of the measurement point among the outlines of the pattern of the photomask to set a measurement area for each group of the two line segments.

16. The pattern measurement system according to claim 15,
wherein the design data managing unit stores a standard pattern corresponding to the OPC processed photomask pattern, and
the control device sets a standard dimension with respect to the standard pattern to select the group of two line segments in an area of the standard dimension.

17. The pattern measurement method according to claim 16,
wherein the standard pattern is obtained by magnifying data of the pattern of the photomask without the OPC processing at a predetermined magnification.

* * * * *